United States Patent [19]

Rubinsztajn et al.

[11] Patent Number: 5,777,144
[45] Date of Patent: Jul. 7, 1998

[54] BI-FUNCTIONAL SILOXANE COMPOUNDS

[75] Inventors: Slawomir Rubinsztajn, Niskuyuna; Gary M. Lucas, Scotia; Brian P. Bayly, Middle Grove, all of N.Y.

[73] Assignee: General Electric Company, Waterford, N.Y.

[21] Appl. No.: 940,589

[22] Filed: Sep. 30, 1997

[51] Int. Cl.$^6$ ............................................. C07F 7/10
[52] U.S. Cl. ............................................................. 556/407
[58] Field of Search .................................................. 556/407

[56] References Cited

U.S. PATENT DOCUMENTS

| | | |
|---|---|---|
| 4,537,944 | 8/1985 | Imai et al. |
| 4,804,771 | 2/1989 | Pepe ............................ 556/407 |
| 4,863,992 | 9/1989 | Wengrovius et al. |
| 5,239,099 | 8/1993 | King et al. ................... 556/407 |
| 5,281,736 | 1/1994 | Tachikawa .................... 556/407 |

*Primary Examiner*—Paul F. Shaver
*Attorney, Agent, or Firm*—Kenneth S. Wheelock

[57] ABSTRACT

Silicon compounds containing the 1-sila-azacyclopentane structure function as alcohol scavengers in one-part alkoxy curing room temperature vulcanizable silicone compositions and the alcohol reaction products of these compounds function as adhesion promoters.

21 Claims, No Drawings

BI-FUNCTIONAL SILOXANE COMPOUNDS

FIELD OF THE INVENTION

The present invention relates to new siloxane compositions of matter wherein the siloxane composition functions both as an alcohol scavenger and as an adhesion promoter in room temperature vulcanizable silicone formulations.

BACKGROUND OF THE INVENTION

The present invention relates to a polyorganosiloxane composition. More particularly the present invention relates to room temperature curable polyorganosiloxane compositions that are rendered stable under moisture free hermetically sealed closed conditions and which cure upon contact with water present in ambient air at room temperature to form an elastomeric composition.

Among polyorganosiloxane compositions that cure at room temperature to form elastomers, one-package or one-part types that cure upon contact with water, however the water is delivered, have been widely used as elastic adhesives or coating agents in the electrical and electronic industries. Also such compositions have been used as sealants in the construction industry since they necessitate none of the troublesome steps involving the measuring and weighing of the quantities of silicones, cross-linking agents, catalysts and mixing and preparing the sealant. Because one-part compositions avoid these steps, the materials are convenient to use and reproducible in their properties.

These one-part compositions comprise a silanol terminated polydiorganosiloxane and a cross-linking agent having more than two hydrolyzable groups per molecule. Upon curing, they generally release acetic acid, a long chain carboxylic acid, an organic amine, an organic amide, an organic hydroxylamine, an organic oxime, an alcohol or acetone depending on the chemical structure of the cross-linking agent employed.

A composition that releases acetic acid, while it generally possesses excellent adhesion and cures quickly, has an offensive and irritating odor. Further, the acetic acid released is frequently corrodes metals when the sealant is used to create a seal between a metal and another substrate. While the odor problems are not as significant with long chain carboxylic acids, the corrosion problems still occur. Compositions that cure by means of releasing an amine present toxicity issues as well as causing odor. Compositions that cure through the release of hydroxylamine, oximes or amides still corrode metals because these types of compounds are known metal ligands and form complexes which is the mechanism of corrosion. Compositions that cure by releasing acetone suffer from yellowing and the cross-linking agents are not convenient to prepare.

Room temperature vulcanizable compositions that cure by releasing alcohols offer a certain convenience because alkoxysilanes are used as the cross-linking agents. The compounds released by curing are alcohols and these generally present no odor or toxicity problems. Alkoxy curing compositions do suffer from a slow cure rate and are very easy to hydrolyze, that is very small amounts of water trigger the curing reaction. This leads to problems with storage of the compositions.

U.S. Pat. Nos. 4,537,944 and 4,760,123 disclose the use of certain silazane compounds as alcohol scavengers that mitigate some of the problems associated with alkoxy based formulations. These patents disclose alcohol scavenging compounds that contain a silicon-nitrogen bond and when reacted with alcohol form a non-volatile nitrogen containing compound. Thus, these types of compounds also tend to reduce the amount of corrosion observed when room temperature vulcanizable sealants are used to seal metals. The silicon nitrogen compounds that have been found to be particularly useful are those containing a silicon nitrogen bond wherein the nitrogen is bonded indirectly to the same or another silicon by or through one or more carbon atoms.

These compounds are typically prepared by the following reaction scheme:

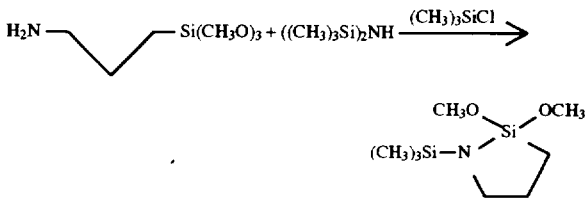

which reacts further to generate the active oligomeric species:

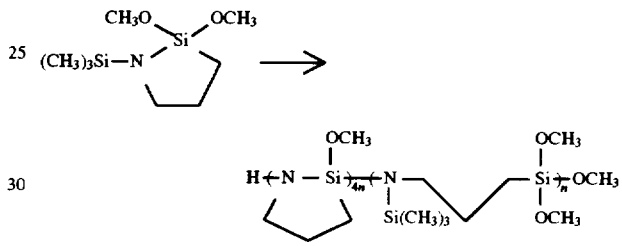

albeit in yields below 50% based on the starting aminoalkoxysilane. A significant problem associated with these compounds is the very toxic nature of the 1,1-dimethoxy-2-trimethylsilyl-1-sila-azacyclopentane:

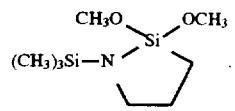

SUMMARY OF THE INVENTION

We now disclose that polymer compounds containing the 1-sila-azacyclopentane structure not only function as alcohol scavengers in one-part alkoxy curing room temperature vulcanizable silicone compositions the alcohol reaction products of these compounds also function as adhesion promoters.

Thus the present invention provides for a silicon containing compound comprising a monovalent functional group having the structure:

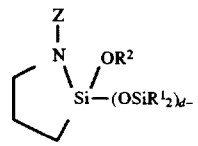

where Z is selected from the group of monovalent radicals consisting of $SiR''_3$, —$(CH2)_p(CR^1R^2)_{m-p}NH_t(SiR''_3)_{2-t}$ and —$(CH_2)_p(CR^1R^2)_{m-p}HN(CH_2)_q(CR^1R^2)_{r-q}NH_t(SiR''_3)_{2-t}$ where each $R^1$, each $R^2$ and each $R''$ are independently a monovalent hydrocarbon radical having from one to forty carbon atoms; each t is independently 0, 1, or 2; each m and each r independently range from 1 to 8; each p ranges from zero to m and each q independently ranges from zero to r; and the subscript d ranges from 1 to about 1,000.

Because an alternative mode of expressing the compounds of the present invention involves expressing them as a reaction product of specific precursors, the present invention also provides for the reaction product of the reaction between a disilazane having the formula R"$_3$SiNHSiR"$_3$ and (R$^3$$_{2-t}$H$_t$N(CH$_2$)$_p$(CR$^1$R$^2$)$_{m-p}$)$_v$H$_{2-v}$N(CH$_2$)$_q$(CR$^1$R$^2$)$_{r-q}$Si (OR2)$_2$(SiR$^1$$_2$O)$_d$Si(OR2)2(CR$^1$R$^2$)$_{r-q}$(CH$^2$)$_q$NH$_{2-v}$(CR$^1$R$^2$)$_{m-p}$(CH$_2$)$_p$NH$_t$R$^3$$_{2-t}$)$_v$ where each R$^1$, each R$^2$ and each R" are independently a monovalent hydrocarbon radical having from one to forty carbon atoms; R$^3$ is selected from the group of monovalent radicals consisting of R$^1$ and —(CR$^1$R$^2$)$_{m-p}$(CH$_2$)$_p$NH$_u$R$^1$$_{2-u}$; each t, each u, and each v are independently 0, 1, or 2; each m and each r independently range from 1 to 8; each p ranges from zero to m and each q independently ranges from zero to r; and the subscript d ranges from 1 to about 1,000.

DETAILED DESCRIPTION OF THE INVENTION

The compounds of the present invention are prepared by the following reaction scheme:
HO(SiR$^1$$_2$O)$_n$H+2H$_2$N(CH$_2$)$_m$Si(OR$^2$)$_3$→H$_2$N(CH$_2$)$_m$Si(OR$^2$)$_2$(SiR$^1$$_2$O)$_n$Si(OR$_2$)$_2$(CH$_2$)$_m$NH$_2$; which involves the reaction between an amino alkoxy silane where the alkyl group has a length varying by the number of methylene groups present in the molecule, represented by the stoichiometric subscript m, where m is preferably 3 or 4 but may range from 1 to 8 and a polymeric diorganosiloxane where the degree of polymerization is indicated by the stoichiometric subscript n which ranges from about 1 to about 1,000, preferably from about 1 to about 100, more preferably from about 1 to about 50, and most preferably from about 2 to about 15 in the presence of catalytic amounts of an acid compound preferably a carboxylic acid, e.g. formic or acetic. This reaction is well characterized and is taught in greater detail in U.S. Pat. No. 4,863,992 herewith incorporated by reference. The R groups, R$^1$ and R$^2$, may be any of several monovalent hydrocarbon radicals known in the art and are preferably selected from the group of monovalent hydrocarbon radicals having from one to forty carbon atoms which may be aliphatic or aromatic and which may be substituted with halogens such as fluorine, chlorine or bromine. While the amino alkoxy silanes employed as starting materials will most generally be simply molecules that vary in the number of divalent methylene groups, CH$_2$, the methylene groups may be substituted with other monovalent hydrocarbon radicals selected from the same group as for R$^1$ and R$^2$. Thus a more general formula for the starting amino alkoxy silane is H$_2$N(CH$_2$)$_p$(CR$^1$R$^2$)$_{m-p}$Si(OR$^2$)$_3$ where each are R$^1$ and R$^2$ are independently selected and the subscript p is an integer which ranges from zero to m. Other amino alkoxy silanes may also be used such as H$_2$N(CH$_2$)$_p$ (CR$^1$R$^2$)$_{m-p}$HN(CH$_2$)$_q$ (CR$^1$R$^2$)$_{r-q}$Si(OR$^2$)$_3$ where q and r may independently assume the same values as p and m respectively. Di- and tri-substituted amino alkoxysilanes of the formula R$^3$$_{2-t}$H$_t$N(CH$_2$)$_p$(CR$^1$R$^2$)$_{m-p}$HN(CH$_2$)$_q$ (CR$^1$R$^2$)$_{r-q}$Si(OR$^2$)$_3$ may also be used where R$^3$ is selected from the group of monovalent radicals consisting of R$^1$ and —(CR$^1$R$^2$)$_{m-p}$(CH$_2$)$_p$NH$_u$R$^1$$_{2-u}$ where t and u are independently 0, 1, or 2. It should be noted that additional generalization of the reaction scheme is possible.

The second step of the preparation of the compounds of the present invention is the following reaction:

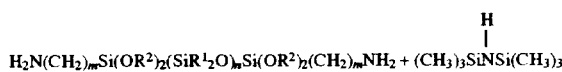

in the presence of trace amounts of alkyl halosilanes, e.g. (CH$_3$)$_3$SiCl, or other acidic catalysts, e.g. Bronsted acids or the ammonium salts of strong Bronsted acids to yield:

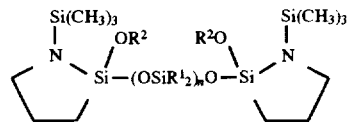

as well as similar products from the higher order amino compounds R$^3$$_{2-t}$H$_t$N(CH$_2$)$_p$(CR$^1$ R$^2$)$_{m-p}$HN(CH$_2$)$_q$ (CR$^1$R$^2$)$_{r-q}$Si(OR$^2$)$_3$ such as for example:

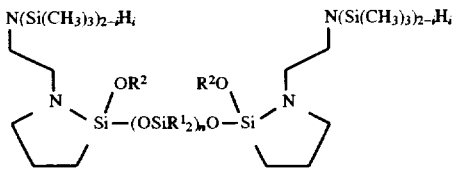

and higher order oligomers following the general scheme of condensation indicated by these products:

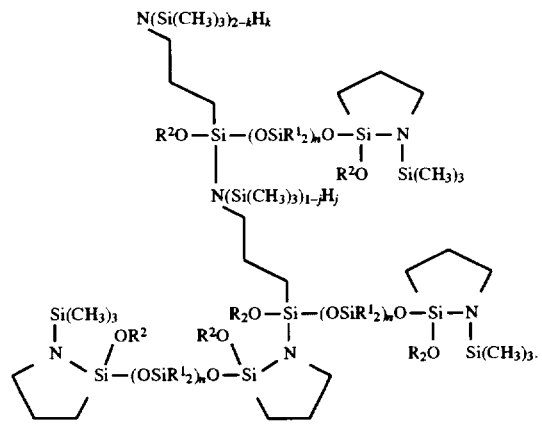

In the structures above j is 0 or 1 and i or k is 0, 1 or 2. The index n will be governed by the species used as a starting material as will the R$^1$ and R$^2$ substituents. The index d has the same values as the index n. Use of other hexa-organo-disilazanes will result in the substitution of other organo groups for the methyl group in the 1-sila-azacyclopentane structures. Thus the compounds of the present invention comprise a 1-sila-azacyclopentane functionalized siloxane comprising a monovalent 1-sila-azacyclopentane moiety having the structure:

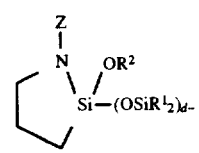

where the subscript d ranges about 1 to about 1,000, preferably from about 1 to about 100, more preferably from about 1 to about 50, and most preferably from about 2 to about 15. R$^1$, R$^2$ and R" may be any of several monovalent hydrocarbon radicals known in the art and are preferably selected from the group of monovalent hydrocarbon radicals having from one to forty carbon atoms which may be aliphatic or aromatic and which may be substituted with halogens such as fluorine, chlorine or bromine and Z is a monovalent radical selected from the group consisting of SiR"$_3$, —(CH$_2$)$_p$(CR$^1$R$^2$)$_{m-p}$NH$_t$(SiR"$_3$)$_{2-t}$, and —(CH$_2$)$_p$(CR$^1$R$^2$)$_{m-p}$HN(CH$_2$)$_q$(CR$^1$R$^2$)$_{r-q}$NH$_t$(SiR"$_3$)$_{2-t}$, where m and r each independently range from 1 to 8 and p and q each independently range from zero to m or r and t is 0, 1, or 2. R$^1$, R$^2$ and R" are preferably selected from the group of monovalent hydrocarbon radicals consisting of methyl, ethyl, propyl, iso-propyl, trifluoropropyl, n-butyl, sec-butyl, t-butyl, phenyl, and tolyl. Thus generally the compounds of the present invention are also reaction products of the reaction between a disilazane having the formula R"$_3$SiNHSiR"$_3$ and (R$^3{}_{2-v}$H$_v$N(CH$_2$)$_p$(CR$^1$R$^2$)$_{m-p}$)$_x$H$_{2-x}$N(CH$_2$)$_q$(CR$^1$R$^2$)$_{r-q}$Si(OR$^2$)$_2$(SiR$^1{}_2$O)$_a$Si(OR$^2$)$_2$(CR$^1$R$^2$)$_{r-q}$(CH$^2$)$_q$NH$_{2-v}$((CR$^1$R$^2$)$_{m-p}$(CH$_2$)$_p$NH$_v$R$^3{}_{2-t}$)$_v$ where R$^3$ is selected from the group of monovalent radicals consisting of R$^1$ and —(CR$^1$R$^2$)$_{m-p}$(CH$_2$)$_p$NH$_u$R$^1{}_{2-u}$where t and u are independently 0,1, or 2.

The compounds of the present invention function sequentially, first as alcohol scavengers and as the compound undergoes alcoholysis it is converted to species that function as adhesion promoters in room temperature vulcanizable compositions due to the presence of the 1-sila-azacyclopentane moiety.

All United States patents referenced herein are herewith and hereby specifically incorporated by reference.

Experimental

The following preparations are illustrative of the invention and are not intended to limit the scope of the appended claims.

Synthesis of aminofunctionalized diorganopolysiloxane

To a three necked round bottom flask equipped with a stirrer, thermometer and condenser was added 40 g of a disilanol stopped polydimthylsiloxane (silanol stopped PDMS) having an approximate value of 6 for n, to which was added 27 g of aminopropyltrimethoxysilane (m=3, R$^2$=CH$_3$). After mixing, 2 drops, approximately 0.10 ml, of 80% aqueous formic acid was added and the reaction mixture was heated to 60° C. for one hour. The reaction mixture was stripped of unreacted starting materials by heating to 120° C. under a vacuum of 20 mm Hg, which removed methanol and unreacted aminosilane. 60 g of a clear and colorless low viscosity fluid, 20–40 cSt, was obtained. Nuclear magnetic resonance analysis confirmed existence of a linear polymer, A, with aminoalkyl substituents on the terminal silicon atoms of the polymer. Gas chromatographic analysis of the product indicated the presence of no more than 1% unreacted aminopropyltrimethoxysilane.

Preparation of sila-aza-cyclopentane compounds

To a three necked round bottom flask equipped with a stirrer, thermometer and condenser was added 60 g of polymer A, prepared above, 32 g of hexamethyldisilazane, and 0.5 g of trimethylchlorosilane. The reaction mixture was heated slowly to 100° C. When the reaction mixture reached 100° C., a significant amount of ammonia was evolved accompanied by the distillation of trimethylmethoxysilane. After 8 hours the reaction mixture was stripped of volatiles at 100° C. and 20 mm Hg, yielding 64 g of a light yellow fluid having a viscosity of 130 cSt. Nuclear magnetic resonance (nmr) analysis indicated disappearance of the N—H group and $^{29}$Si nmr indicated the presence of N—Si(CH$_3$)$_3$ groups.

Preparation of sila-aza-cyclopentane compounds— Substitution of Ammonium Sulfate for Trimethylchlorosilane To a three necked round bottom flask equipped with a stirrer, thermometer and condenser was added 60 g of polymer A, as prepared above, 32 g of hexamethyldisilazane, and 0.9 g of ammonium sulfate. The reaction mixture was heated slowly to 100° C. When the reaction mixture reached 100° C., a significant amount of ammonia was evolved accompanied by the distillation of trimethylmethoxysilane. After 8 hours the reaction mixture was stripped of volatiles at 100° C. and 20 mm Hg, yielding 64 g of a light yellow fluid having a viscosity of 120 cSt. Nuclear magnetic resonance (nmr) analysis indicated disappearance of the N—H group and $^{29}$Si nmr indicated the presence of N—Si(CH$_3$)$_3$ groups.

These preparations have been repeated using aminopropyltrimethoxysilane (methoxyGAP), aminopropyltriethoxysilane (ethoxyGAP) and aminoethylaminopropyltrimethoxysilane (AEAPTMS). The sila-aza-cyclopentane compounds prepared from these starting materials are listed in Table 1.

TABLE 1

Sila-aza-cyclopentane endcapped siloxane compounds

| Experiment Number | Amino-silane | PDMS - silanol-stopped, wt. in g | Yield, g | Viscosity, cSt | Comments |
|---|---|---|---|---|---|
| 55 | Methoxy-GAP | 40 | 64 | 130 | light yellow |
| 56 | Methoxy-GAP | 40 | 61 | 120 | light yellow-overheated |
| 59 | AEAPTMS | 37 | 61 | 620 | dark yellow |
| 60 | AEAPTMS | 37 | 58 | 420 | orange |
| 65 | Ethoxy-GAP | 39 | 62 | 130 | light yellow |
| 130 | AEAPTMS | 37 | 60 | 400 | orange |

The compounds prepared in Table 1 were formulated into a variety of different neutral cure RTV formulations and compared against standard neutral cure RTV formulations to demonstrate both the alcohol scavenging ability of the compounds and their function as an adhesion promoter. The formulations are presented in Table 2. Preparation 59 has been overheated with the result that it has a high viscosity and a dark color by comparison to preparations 60 and 130.

TABLE 2

Neutral Cure RTV Formulations using Sila-aza-cyclopentane Compounds

| RTV Inputs | A wt. in g | B wt. in g | C wt. in g | D wt. in g | E wt. in g | F wt. in g | G wt. in g | H wt. in g |
|---|---|---|---|---|---|---|---|---|
| PDMS-1 | 65.4 | 65.4 | 65.4 | 65.4 | 65.4 | 65.4 | 65.4 | 65.4 |
| Fumed Silica | 13 | 13 | 13 | 13 | 13 | 13 | 13 | 13 |

TABLE 2-continued

Neutral Cure RTV Formulations using Sila-aza-cyclopentane Compounds

| RTV. Inputs | A wt. in g | B wt. in g | C wt. in g | D wt. in g | E wt. in g | F wt. in g | G wt. in g | H wt. in g |
|---|---|---|---|---|---|---|---|---|
| CETMS | 0.7 | 0.7 | 0.7 | 0.7 | 0.7 | 0.7 | 0.7 | 0.7 |
| PDMS-II | 10.3 | 10.3 | 10.3 | 10.3 | 10.3 | 10.3 | 10.3 | 10.3 |
| PDMS-SIOH | 4.5 | 4.5 | 4.5 | 4.5 | 4.5 | 4.5 | 4.5 | 4.5 |
| Me(MeO)3Si | 1 | 1 | 1 | 1 | 1 | 1 | 1 | 1 |
| epoxy-Si | 0.25 | 0.25 | 0.25 | 0.25 | 0.25 | 0.25 | 0.25 | 0.25 |
| Tin catalyst | 0.24 | 0.24 | 0.24 | 0.24 | 0.24 | 0.24 | 0.24 | 0.24 |
| HMDZ | 2 | 0 | 0 | 0 | 0 | 0 | 0 | 0 |
| 55 | 0 | 4 | 0 | 0 | 0 | 0 | 0 | 0 |
| 56 | 0 | 0 | 4 | 0 | 0 | 0 | 0 | 0 |
| 59 | 0 | 0 | 0 | 4 | 0 | 0 | 0 | 0 |
| 60 | 0 | 0 | 0 | 0 | 4 | 0 | 0 | 0 |
| 65 | 0 | 0 | 0 | 0 | 0 | 4 | 0 | 0 |
| 130 | 0 | 0 | 0 | 0 | 0 | 0 | 4 | 0 |
| A-577 | 0 | 0 | 0 | 0 | 0 | 0 | 0 | 2 |

As indicated in Table 2, the neutral cure RTV sealant compositions were prepared from the following materials:

PDMS-I is a methyldimethoxy terminated polydimethylsiloxane having a viscosity of 30,000 centipoise at 25° C.;

Fumed Silica is a fumed silica that has been treated with octamethylcylcotetrasiloxane;

CETMS is cynaoethyltrimethoxysilane; PDMS-II is a trimethyl terminated polydimethylsiloxane having a viscosity of 100 cps at 25° C.;

PDMS-SIOH is an M.D.T silanol functional fluid having a viscosity of 50 cps at 25° C.;

Me(MeO)3Si is methyltrimethoxysilane;

epoxy-Si is glycidoxypropyltrimethoxysilane; the tin catalyst is dibutyl tin diacetate;

A-577 is an oligomeric silazane, a product of oligomerization of 1,1-dimethoxy -2-trimethylsilyl-1-silaazacyclopentane; and HMDZ is hexamethyldisilazane.

The neutral cure RTV compositions summarized in Table 2 were evaluated for physical properties after a 7 day cure (Table 3), after 24 hours at 100° C. accelerated shelf storage followed by a 7 day cure (Table 4) and for adhesion after a 7 day cure (Table 5). It should be noted that the overheated preparation 59 gave poor results by comparison to the properly prepared preparations 60 and 130.

TABLE 3

Physical Properties of Neutral Cure RTV Sealants after 7 Day Cure

| RTV | A | B | C | D | E | F | G | H |
|---|---|---|---|---|---|---|---|---|
| E-63 TFT, min. | 15 | 15 | 15 | poor cure | 15 | 15 | 15 | 15 |
| E-2, Shore A | 24 | 31 | 29 | | 28 | 26 | 30 | 32 |
| E-1, Tensile psi | 271 | 305 | 307 | | 337 | 291 | 352 | 233 |
| E-1 Elong., % | 270 | 290 | 295 | | 316 | 294 | 351 | 241 |
| Color | clear | clear | clear | yellow | yellow | clear | yellow | clear |

The fact that materials containing the sila-aza-cyclopentane stopped polydiorganosiloxane cured indicates that the materials are functioning as alcohol scavengers.

TABLE 4

Physical Properties of Neutral Cure RTV Sealants after 24 Hours at 100° C. Accelerated Shelf Storage Plus 7 Day Cure

| RTV | A | B | C | D | E | F | G | H |
|---|---|---|---|---|---|---|---|---|
| E-63 TFT, min. | 15 | 15 | 15 | poor cure | 15 | 15 | 15 | 15 |
| E-2, Shore A | 24 | 31 | 24 | | 27 | 22 | 27 | 29 |
| E-1, Tensile psi | 271 | 266 | 236 | | 301 | 312 | 277 | 258 |
| E-1 Elong., % | 270 | 257 | 248 | | 285 | 354 | 295 | 302 |

TABLE 5

Adhesion Data (7 day cure - ppi, % Cohesive Failure)

| RTV | A | B | C | D | E | F | G | H |
|---|---|---|---|---|---|---|---|---|
| Glass | 1,0 | 28,100 | 32,100 | poor cure | 34,100 | 32,100 | 33,100 | 27,100 |
| Anodized Al | 7,0 | 24,100 | 30,100 | | 36,100 | 29,100 | 26,100 | 35,100 |
| MF Al | 5,0 | 29,100 | 31,100 | | 37,100 | 24,100 | 35,100 | 25,100 |
| PVC | 11,0 | 33,100 | 29,100 | | 41,100 | 26,100 | 31,100 | 27,100 |

Even though glycidoxypropyltrimethoxysilane is present in all formulations and normally functions as an adhesion promoter, the data for composition A clearly show that adhesion was not promoted with these formulations because the percent cohesive failure was zero against all substrates. These data also indicate that after the sila-aza-cyclopentane stopped polydiorganosiloxane react with alcohol to act as an alcohol scavenger, the reaction product of the alcohol scavenging reaction acts as an adhesion promoter.

In order to conclusively demonstrate that the 1-sila azacyclopentane compounds of the present invention act a adhesion promoters independently of the presence of glyci doxypropyltrimethoxysilane neutral cure room temperatur vulcanizable silicone compositions were prepared wherein the glycidoxypropyltrimethoxysilane was absent. Table 6, and the cured properties are summarized in tables 7, 8 and 9.

TABLE 6

Neutral Cure RTV Formulations using Sila-aza-cyclopentane Alcohol Scavenger Compounds Without Additional Adhesion Promoters

| RTV. | I | J | K |
|---|---|---|---|
| Inputs | wt. in g | wt. in g | wt. in g |
| PDMS-I | 66.26 | 66.26 | 66.26 |
| Fumed Silica | 13 | 13 | 13 |
| CETMS | 0.7 | 0.7 | 0.7 |
| PDMS-II | 10.3 | 10.3 | 10.3 |
| PDMS-SIOH | 4.5 | 4.5 | 4.5 |
| Me(MeO)3Si | 1 | 1 | 1 |
| epoxy-Si | 0 | 0 | 0 |
| Tin catalyst | 0.24 | 0.24 | 0.24 |
| HMDZ | 0 | 0 | 0 |
| 55 | 4 | 0 | 0 |
| 56 | 0 | 0 | 0 |
| 59 | 0 | 0 | 0 |
| 60 | 0 | 4 | 0 |
| 65 | 0 | 0 | 4 |

TABLE 7

Physical Properties of Neutral Cure RTV Sealants (no glycidoxypropyltrimethoxysilane) after 7 Day Cure

| RTV | I | J | K |
|---|---|---|---|
| E-63 TFT, min. | 15 | 15 | 15 |
| E-2, Shore A | 23 | 26 | 24 |
| E-1, Tensile psi | 281 | 321 | 284 |
| E-1 Elong., % | 321 | 329 | 318 |

TABLE 8

Physical Properties of Neutral Cure RTV Sealants (no glycidoxypropyltrimethoxysilane) after 24 Hours at 100° C. Accelerated Shelf Storage Plus 7 Day Cure

| RTV | I | J | K |
|---|---|---|---|
| E-63 TFT, min. | 15 | 15 | 15 |
| E-2, Shore A | 25 | 24 | 22 |
| E-1, Tensile psi | 279 | 309 | 267 |
| E-1, Elong., % | 302 | 298 | 307 |

TABLE 9

Adhesion Data of Neutral Cure RTV Sealants (no glycidoxypropyltrimethoxysilane) (7 day cure - ppi, % Cohesive Failure)

| RTV | I | J | K |
|---|---|---|---|
| Glass | 32,100 | 30,100 | 29,100 |
| Anodized Al | 35,100 | 39,100 | 25,100 |
| MF Al | 29,100 | 29,100 | 35,100 |
| PVC | 29,100 | 34,100 | 38,100 |

Having described the invention that which is claimed is:

1. A silicon containing compound comprising a monovalent functional group having the structure:

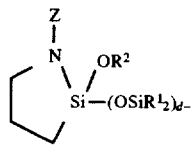

where Z is selected from the group of monovalent radicals consisting of $SiR''_3$, $-(CH2)_p(CR^1R^2)_{m-p}NH_t(SiR''_3)_{2-t}$ and $-(CH_2)_p(CR^1R^2)_{m-p}HN(CH_2)_q(CR^1R^2)_{r-q}NH_t(SiR''_3)_{2-t}$ where each $R^1$, each $R^2$ and each R'' are independently a monovalent hydrocarbon radical having from one to forty carbon atoms; each t is independently 0, 1, or 2; each m and each r independently range from 1 to 8; each p ranges from zero to m and each q independently ranges from zero to r; and the subscript d ranges from 1 to about 1,000.

2. The compound of claim 1 where $R^1$, $R^2$ and R'' are selected from the group of monovalent hydrocarbon radicals consisting of methyl, ethyl, propyl, iso-propyl, trifluoropropyl, n-butyl, sec-butyl, t-butyl, phenyl, and tolyl.

3. The compound of claim 2 where $R^1$ is methyl.

4. The compound of claim 3 where $R^2$ is methyl.

5. The compound of claim 4 where $R^3$ is methyl.

6. The compound of claim 1 where the subscript d ranges from 1 to about 100.

7. The compound of claim 6 where $R^1$ is methyl.

8. The compound of claim 7 where $R^2$ is methyl.

9. The compound of claim 8 where $R^3$ is methyl.

10. The compound of claim 1 where the subscript d ranges from 1 to about 50.

11. The compound of claim 1 where the subscript d ranges from about 2 to about 15.

12. The compound of claim 11 where $R^1$ is methyl.

13. The compound of claim 12 where $R^2$ is methyl.

14. The compound of claim 13 where $R^3$ is methyl.

15. A silicon containing compound comprising two monovalent functional groups having the structure:

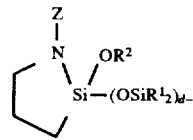

where Z is selected from the group of monovalent radicals consisting of $SiR''_3$, $-(CH2)_p(CR^1R^2)_{m-p}NH_t(SiR''_3)_{2-t}$ and $-(CH_2)_p(CR^1R^2)_{m-p}HN(CH_2)_q(CR^1R^2)_{r-q}NH_t(SiR''_3)_{2-t}$ where each $R^1$, each $R^2$ and each R'' are independently a monovalent hydrocarbon radical having from one to forty carbon atoms; each t is independently 0, 1, or 2; each m and each r independently range from 1 to 8; each p wanges from zero to m and each q independently ranges from zero to r; and the subscript d ranges from 1 to about 1,000.

16. The compound of claim 15 where $R^1$, $R^2$ and R'' are selected from the group of monovalent hydrocarbon radicals consisting of methyl, ethyl, propyl, iso-propyl, trifluoropropyl, n-butyl, sec-butyl, t-butyl, phenyl, and tolyl.

17. The compound of claim 16 where $R^1$ is methyl.

18. The compound of claim 17 where $R^2$ is methyl.

19. The compound of claim 18 where $R^3$ is methyl.

20. A silicon containing compound comprising three monovalent functional groups having the structure:

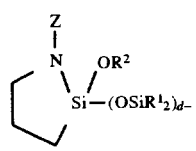

where Z is selected from the group of monovalent radicals consisting of $SiR''_3$, $-(CH_2)_p(CR^1R^2)_{m-p}NH_t(SiR''_3)_{2-t}$ and $-(CH_2)_p(CR^1R^2)_{m-p}HN(CH_2)_q(CR^1R^2)_{r-q}NH_t(SiR''_3)_{2-t}$ where each $R^1$, each $R^2$ and each $R''$ are independently a monovalent hydrocarbon radical having from one to forty carbon atoms; each t is independently 0, 1, or 2; each m and each r independently range from 1 to 8; each p ranges from zero to m and each q independently ranges from zero to r; and the subscript d ranges from 1 to about 1,000.

21. The reaction product of the reaction between a disilazane having the formula $R''_3SiNHSiR''_3$ and $(R^3_{2-t}H_tN(CH_2)_p(CR^1R^2)_{m-p})_vH_{2-v}N(CH_2)_q(CR^1R^2)_{r-q}Si(OR^2)_2(SiR^1_2O)_dSi(OR^2)_2(CR^1R^2)_{r-q}(CH^2)_qNH_{2-v}((CR^1R^2)_{m-p}(CH_2)_pNH_tR^3_{2-t})_v$ where each $R^1$, each $R^2$ and each $R''$ are independently a monovalent hydrocarbon radical having from one to forty carbon atoms; $R^3$ is selected from the group of monovalent radicals consisting of $R^1$ and $-(CR^1R^2)_{m-p}(CH_2)_pNH_uR^1_{2-u}$; each t, each u, and each v are independently 0, 1, or 2; each m and each r independently range from 1 to 8; each p ranges from zero to m and each q independently ranges from zero to r; and the subscript d ranges from 1 to about 1,000.

* * * * *